US006538125B2

(12) United States Patent
Hasebe et al.

(10) Patent No.: US 6,538,125 B2
(45) Date of Patent: Mar. 25, 2003

(54) INSERTION SEQUENCE ELEMENT DERIVED FROM RALSTONIA SOLANACEARUM

(75) Inventors: Akira Hasebe, Ibaraki-Pref. (JP); Kenichi Tsuchiya, Ibaraki-Pref. (JP); Mitsuo Horita, Chiba-Pref. (JP)

(73) Assignee: National Institute of Agrobiological Sciences (JP)

( * ) Notice: Subject to any disclaimer, the term of this patent is extended or adjusted under 35 U.S.C. 154(b) by 0 days.

(21) Appl. No.: 10/222,577

(22) Filed: Aug. 16, 2002

(65) Prior Publication Data

US 2003/0009026 A1 Jan. 9, 2003

Related U.S. Application Data

(62) Division of application No. 09/790,045, filed on Feb. 21, 2001, now Pat. No. 6,492,510.

(30) Foreign Application Priority Data

Oct. 11, 2000 (JP) ....................................... 2000-310193
Jun. 22, 2000 (JP) ....................................... 2000-187855

(51) Int. Cl.$^7$ ................................................ C12N 15/31
(52) U.S. Cl. ...................................................... 536/23.7
(58) Field of Search ......................................... 536/23.7

(56) References Cited

FOREIGN PATENT DOCUMENTS

| | | |
|---|---|---|
| JP | 2182440 | 6/1999 |
| JP | 2188350 | 11/1999 |
| JP | 2188351 | 7/2000 |
| JP | 2188352 | 10/2000 |

OTHER PUBLICATIONS

AB050447 EMBL Database.

Werner Arber, et al., Generation of genetic diversity by DNA rearrangement in resting Bacteria, Fems Microbiology Ecology, 15 (1994) 5–14.

P. Gay, et al., Positive Selection Procedure for Entrapment of Insertion Sequence Elements in Gram–Negative Bacteria, Journal of Bacteriology, Nov. 1985, at 918–921.

Jacques Mahillon and Michael Chandler, Insertion Sequences, Microbiology and Molecular Biology Reviews, Sep. 1998, at 725–774.

Douglas E. Berg and Martha M. Howe, Mobile DNA at 109 (1989).

Isabel Otal, et al., Restriction Fragment Length Polymorphism Analysis Using IS6110 as an Epidemiological Marker in Tuberculosis, Journal of Clinical Microbiology, Jun. 1991, at 1252–1254.

Dieter Haas, et al., Molecular Biology of Pseudomonads, 239 (1996).

Akira Hasebe, et al., Isolation and Characterization of IS1416 from Pseudomonas gluae, a New Member of the IS3 Family, PLASMID 39, (1998) at 196–204.

Tore–Geir Iversen, et al., IS1032 from Acetobacter xylinum, a New Mobile Insertion Sequence, PLASMID 32, (1994) at 46–54.

H. Saedler and A. Gierl, Transposable Elements., Ohtsubo and Sekine, Bacterial Insertion Sequences, 1–26 (1996).

European Search Report (6 Documents included as follows:).

Mahillon, Jacques, et al. "IS elements as constituents of bacterial genomes," Res. Microbiol. 150 (1999) 675–687.

Jeong, E. L. and Timmis, J.N. "Novel Insertion Sequence Elements Associated with Genetic Heterogeneity and Phenotype Conversion in Ralstonia solanacearum," Journal of Bacteriology Aug. 2000, 4673–4676.

AB028897 EMBL Database.

AF186082 EMBL Database.

AB045355 EMBL Database.

*Primary Examiner*—Terry McKelvey
(74) *Attorney, Agent, or Firm*—Amin & Turocy, LLP

(57) ABSTRACT

The present invention provides three insertion elements and transposases encoded by the insertion elements that are derived from the genome of Ralstonia solanacearum, which has been isolated with a transposon trap vector.

2 Claims, 4 Drawing Sheets

```
TTAGGCCGCTAACAAACCAAGTCATCGAACGCAGGTGTTGAGCGCTTGTTGTGGCATGGCACGAAAGAAGATCAGCAATGAACTGTGGAAGGCGTTG   100
                                                         M  A  R  K  K  I  S  N  E  L  W  K  A  L
                                                         ORFA

CAACCGGTGCTGCCGGTTGTGAGCCTTCGACCAAAGGGCGGTCGTTCCGCCGGTGATCGGCGGCGCTGAACGGCATCCTGTTTGTTCTGCATACCG   200
 Q  P  L  L  P  V  V  E  P  S  T  K  G  G  R  P  R  V  D  D  R  A  A  L  N  G  I  L  F  V  L  H  T  G

GTATCCCGTGGGAAGACTGCCTAAAGAACTGGGCTTTGGCAGCGGGCATGACGTGCTGGCGTCGCCTGCGGAGTGGCAGGCCAACGGCGTTTGGGAGCG   300
                ORFB
                 R  T  G  L  W  Q  R  H  D  V  L  A  S  P  A  G  V  A  G  Q  R  R  L  G  A
 I  P  W  E  D  L  P  K  E  L  G  F  G  S  G  M  T  C  W  R  R  L  R  E  W  Q  A  N  G  V  W  E  R

GCTGCATTTGGCTCTGCTCAAGCGGCTGCGGAACACGACAGATCGACTGAGGCGAGCCAGTGTCGACGGTGCAACGGTGGCAGCCCCCGGGGGCG   400
 A  A  F  G  S  A  Q  A  P  A  R  T  R  P  D  R  L  E  P  S  Q  C  R  R  C  N  G  Q  P  P  G  G
 L  H  L  A  L  L  K  R  L  R  E  H  D  Q  I  D  W  S  R  A  S  V  D  G  A  T  V  A  S  P  R  G  A

AGCAGACGGGGCCGAATCCAACGGATCGTGGCAAGCTCGGTAGCAAGCGCCATCTCTGTCGTAGATCGGCGGCGTGCCCTTGGGCGCTGATGGTCACCGG   500
 Q  T  G  P  N  P  T  D  R  G  K  L  G  S  K  R  H  L  V  V  D  R  R  R  G  V  P  L  A  L  M  V  T  G
 S  R  R  G  R  I  Q  R  I  V  A  S  S  V  A  S  S  K  R  H  L  V  V  D  R  R  R  G  V  P  L  A  L  M  V  T  G *
                                                 * A  I  S  S

TGCCAATCGTCACGACTCGGTGGTGTTCGAGGTGCTCGTTGACGCCATCCCGAGCGTGCCCCGGACTCGCCCCCGATGCCGCCCGACAAGCTT   600
 A  N  R  H  D  S  V  V  F  E  V  L  V  D  A  I  P  S  V  P  G  L  D  G  R  P  R  C  R  P  D  K  L

CACGGGGATAAGGGATACGACTTCGGCGAGCGATGCCGTCGCCATCTGCGCAAGCGGCATGACTCCCCGTGGCATCGAGAAGAACGACC   700
 H  A  D  K  G  Y  D  F  A  R  C  R  R  H  L  R  K  R  G  M  T  P  R  I  A  R  R  G  I  E  K  N  D  R

GGCTCGGCAAGCATAAGCGATCCGGCATCGGTTGTCGAGCGCGTCACCATGCCTGGCTTCGGCAAGTTGCGCATTCGTTTCGAGCGTTCTTCAGACTCATCT   800
 H  A  D  K  G  Y  D  F  A  R  C  R  R  H  L  R  K  R  G  M  T  P  R  I  A  R  R  G  I  E  K  N  D  R
 G  L  G  K  H  R  W  V  V  E  R  T  H  A  W  L  A  G  G  F  F  G  K  L  R  I  R  F  E  R  S  L  Q  T  H  L

CGGTTTGCTCACCCTGGCTTGCGCCGTCATCTGCGGGGCCGATCTGTTGATCGGTTTTGTTAGGACTCTTA   870
 A  L  L  T  L  A  C  A  V  I  C  G  G  R  F  V  D  R  F  C *
                                                         ORFC
```

Fig. 3

```
TAA GGGTCAAGGACCCATTGATTTGAATTGACGGCTATGATTCAGATGATGAATTTGTTCTGGCTGACTAACGAGCAA    100
                                                 M  S  N  L  F  W  L  T  N  E  Q
                                                 ORFA
ATGGCTCGTCTTCAGCCCTATTTCCCCAAGAGCCATGGCCGCCAGGTCGTGTCGATCGGGCGTGTCCTGAGCGGCAACGGGC    200
 M  A  R  L  Q  P  Y  F  P  K  S  H  G  R  Q  R  V  D  D  R  R  V  L  S  G  I  I  F  V  N  R  N  G  L

TCCGGTGGTGCGATGCGCCGAAGGAATATGGCCCGGCGAAAACGCTGTATAACCGGTGGAAGCGACAAGGGCATCTTTATCCAGATGATGGA    300
 R  W  C  D  A  P  K  E  Y  G  P  A  K  T  L  Y  N  R  W  K  R  W  S  D  K  G  I  F  I  Q  M  M  D

CGGGCTGGCTGTGCCTGAAGCTGCAGAACACCAGACCGTCATGATTGATGCCAACCTATCTCAAGGCCCACCGCCACGGGTTCGAGCCTGCGGGTAAAAAAG    400
 G  L  A  V  P  E  A  A  E  H  Q  T  V  M  I  D  A  T  Y  L  K  A  H  R  T  A  S  S  L  R  V  K  K  G
                                          ORFB
                                          C  N  L  S  Q  G  P  P  H  G  F  E  P  A  G  K  K  K

GGGCGCGGGTCGCTGATTGGACGTGCGCAAGGGCCTGTGACGGATGAACACCAAGCTTCATGCCCGATGATCAGTTTCTTCATAAC    500
 G  A  G  R  L  I  G  R  T  K  G  G  M  N  T  K  L  H  A  V  T  D  A  S  G  R  P  I  S  F  F  I  T

GGGCCGTCAAATCAGCGATTACACCGGTGCTGCTGCCGGCGCAAATGGCTACTGCCGACCGTGGCCAAGGCCCAAATGGCTACTGCCGACCGTGGCTATGATGCCGACTGG    600
 A  G  Q  I  S  D  Y  T  G  A  A  A  L  L  D  E  L  P  K  A  K  W  L  L  A  D  R  G  Y  D  A  D  W

TATCGTGACGGTTACAGGGCGAAGGGATCACTCCCTGCATTCCCGGTCGGAAATACCGAAGACCATCAAATACGACAAACGGCGCTATAAACGGC    700
 Y  R  D  A  L  Q  A  K  G  I  T  P  C  I  P  G  R  K  S  R  T  T  T  I  K  Y  D  K  R  R  Y  K  R  R

GCAACCGAATAGAGATCATGTTCGGGCGTCTCAAGGATTGGCGACGTGTCGCAGGTGCGATGCCAATGGCTTTCTTTCCGCCATCTCTCT    800
 N  R  I  E  I  M  F  G  R  L  K  D  W  R  R  V  A  T  R  Y  D  R  C  P  M  A  F  L  S  A  I  S  L

CGCTGCAACCGTATCTTCTGGCTCTGATCAACGAGTCCTGACCC TAA                                        848
 A  A  T  V  I  F  W  L  *
```

Fig. 4

```
TAA GAGCCCGTTTGAAAAT CCCCGCCGTTGTGGTGTAAAGGCGGGATGTGGAAAAAGAAGATCGAGAGCGTGAGGCGAAGCTGGCTCGGAAGACCAAG  100
                                              M  W  K  K  E  D  R  E  R  E  A  K  L  A  R  K  T  K
                                              ORFA
CGTTACCCGAGCGACCTGACGGATATCGAATGGGCCGCCGTCGTGCAGCCGCTGCTGCCACGGCCGGCTGCGGAGTGCGACTTGAGGG  200
 R  Y  P  S  D  L  T  D  I  E  W  A  A  V  Q  P  L  L  P  R  A  A  V  R  G  R  R  R  E  C  D  L  R  E
AGGTGGTCAACGGCCTTGGCTATCTCGTGCGAGCGGGGTGCGGCATGCTGCCGCACGACTTCCCGCCTTGGCAAACCGTGTATTGGTTTCG  300
 V  V  N  A  L  R  Y  L  V  R  A  G  C  G  W  R  M  L  P  H  D  F  P  P  W  Q  T  V  Y  W  W  F  R
TCGGCTCATGCGTCGCTTCCTGTTCCGCACGCTGCACGACGTGGTGCTGATGTTGGACCGGGAGTTGGCCGGGAGGCAGCCGTGCCCGAGTGCGGGCGTC  400
 R  L  M  R  R  F  L  F  R  T  L  H  D  V  V  L  M  L  D  R  E  L  A  G  R  Q  P  C  P  S  A  G  V
ATCGACAGCCAGACAGTCAAGGCCCCTCGGCCGGATGCAAGCGGCTACGACGGGCAAGAAATCGTCGGGCGTGTGGACACGG  500
 I  D  S  Q  T  V  K  A  P  S  A  D  K  R  G  Y  D  A  K  K  I  V  G  R  K  R  H  I  A  V  D  T  D
ATGGACGGCTGCTGATGGTGAACCTGACACCGGCCGATATCGCCGATAGCACGGGTGCGCTGGCGGTGCTGGAAGAAGCGCTGAAGAAGCGCTGGCCAGGCAT  600
 M  D  G  L  L  M  V  N  L  T  P  A  D  I  A  D  S  T  G  A  L  A  V  L  E  A  V  K  K  R  W  P  G  I
AAAACACCTGTTCGCTGACGGTGCGTATGACCGACAAGGCATCGATGACCGCACCACGCTTCTGATGGACAAGGCCTCGACCCTTGACTTCGTTGTGGAGGTGGTGCGCCGCCACGAGCAG  700
 K  H  L  F  A  D  G  A  Y  D  R  T  T  L  M  D  K  A  S  T  L  D  F  V  V  E  V  V  R  R  H  E  Q
CAAACGGGCTTTGCCGTTCTGCCGCGCCGCTGGGTGGTGGAGCGGACCTTCGGATGGTTCGTCGACTCGTACGAGCAGCGCG  800
 Q  T  G  F  F  A  V  L  P  R  R  W  V  V  E  R  T  F  G  W  M  V  R  W  R  R  L  V  R  D  Y  E  Q  R  A
CGGACGTCTCGGAAGCCATGATTCATATCGCGATGAGCGGCTTGCTACTGCGCAGAATCGCTCATCCTTGAATTTCCAAACGGGCTCTAA  890
 D  V  S  E  A  M  I  H  I  A  M  S  G  L  L  L  R  R  I  A  H  P  *
```

INSERTION SEQUENCE ELEMENT DERIVED FROM RALSTONIA SOLANACEARUM

CROSS-REFERENCE TO RELATED APPLICATIONS

This application is a divisional of U.S. application Ser. No. 09/790,045, filed Feb. 21, 2001 U.S. Pat. No. 6,492,510.

BACKGROUND OF THE INVENTION

1. Field of the Invention

The present invention relates to a transposable element isolated from the genome of Ralstonia solanacearum and a transposase encoded by the transposable element.

2. Description of the Related Art

It is known that transposable elements not only inactivate or activate genes before and after the transposition site by moving on the genome, but also cause various genome rearrangements such as deletion, inversion and duplication. It is also known that the transposable elements contribute to genome plasticity that is important for the evolution and the environmental adaptation of microorganisms (Arber et al., FEMS Microb. Ecol., 15: 5–14 (1994)).

Transposable elements can be classified into transposons and insertion sequence elements. Transposons are defined as genes involved in transposition and having phenotypic genes such as antibiotic resistances. On the other hand, insertion sequence elements (hereinafter, referred to as IS elements) are defined as genes that generally have a size of 2 kb or less and have no phenotypic genes other than the genes involved in gene transposition (Gay et al., J. Bacteriol., 164: 918–921 (1985)).

The IS element was first discovered in the late 1960's as an element that causes mutation of *E. coli*. Thereafter, the IS elements of *E. coli* in particular were isolated and characterized. In the late 1980's, there were reports of isolation of the IS elements from bacteria other than the *E. coli* group. At present, about 500 IS elements are reported to have been isolated from medical bacteria, environmental bacteria and others (Mahillon et al., Microbiol. Mol. Bio. Rev., 62:725–774(1998)).

The isolated IS elements are compared with each other based on the base sequence and the deduced amino acid sequence. The IS elements that have been found so far are classified into 17 families. Among these families, the IS3 family and the IS5 family are large families, and IS elements belonging to these families are isolated from bacteria ranging widely from Gram-negative bacteria to Gram-positive bacteria (Mahillon et al., ibid.).

The structure of the IS elements in the IS3 and the IS5 families is characterized by the presence of inverted repeat sequences at their terminals and the inclusion of two open reading frames encoding a transposase. It seems that the terminal inverted repeat sequences play an important role in transposition, because recombination occurs in these portions. For example, in insertion, 2 to 13 base pairs in the site where insertion occurs are overlapped as same direct repeat sequences on both sides of the IS element (Galas and Chandler, Mobile DNA, 109–162, ASM Press (Washington, D.C.) 1989).

Transposase is an enzyme that catalyzes an insertion reaction of a gene. In the IS elements of the IS3 family and the IS5 family, the transposase is encoded by two open reading frames and is expressed as one protein in translation. For example, in the case of the IS3 family, two open reading frames overlap, and a frame shift occurs in the overlapping portion. Then, the two open reading frames are translated successively so that the transposase is expressed (Ohtsubo and Sekine, Current topics in Microbiology and Immunology, 204:1–26 (1996)).

Each of the IS elements obtained from various microorganisms has a sequence that is unique to the particular microorganism, although they are homologous. Utilizing the unique sequence, in the industrial fields of agriculture, foods, pharmacy and the like in which microorganisms are involved, the IS elements are used, for example, for identification of plant pathogenic bacteria, diagnosis of infectious diseases, determination of infection routes and isolation of useful genes. The IS element that is most common in practical use is IS6110, which is obtained from Mycobacterium tuberculosis and contributes to epidemiological surveys such as diagnosis of tuberculosis and determination of the infection route (Otal et al., J. Clin. Microbiol., 29:1252–1254 (1991)). Similar attempts have been conducted with various bacteria.

IS elements are characterized by being able to activate or inactivate genes before and after the inserted site by transposition. Utilizing this function positively, it is attempted to use the IS elements as a tool for isolating useful genes (Haas et al., Molecular Biology of Pseudomonas, 238–249, ASM Press (Washington D.C.) (1996)).

The isolation of the IS elements was not conducted strategically, but mostly was rather accidentally achieved by analysis of mutants. This is because, as seen from the definition, IS elements have no phenotype other than involvement in gene transposition, so that positive isolation was difficult. Various transposon trap vectors have been developed since positive selection of the transposable element (a method of utilizing activation of a detectable marker by transposition of the transposable element to a part of a structural gene) was successfully reported in 1985 (Gay et al., ibid.), and the IS elements have been isolated from bacteria such as Agrobacterium tumefaciens, Pseudomonas cepacia, Rhizobium meliloti, Rhizobium legumino sarum or the like by this method.

However, only 20 IS elements were isolated by this method, and this is a small number relative to the total number of the isolated IS elements. The isolation of new IS elements from various bacteria is expected to be accelerated as the positive selection is developed.

In regard to agriculturally important plant-related bacteria, Hasebe et al. isolated three kinds of IS elements from Pseudomonas glumae, which is a common pathogenic bacterium in rice plants in Japan, by utilizing a transposon trap vector pSHI1063 (Hasebe et al., Plasmid, 39:196–204 (1998)) (see Japanese Laid-Open Publication No. 10-248573). However, in reality, isolation of other IS elements has not been substantially researched. Isolation of IS elements of various plant pathogenic bacteria (microorganisms) makes it possible to counter the pathogenic bacteria, so that there is a demand for isolation and utilization of the IS elements in the field of agriculture.

SUMMARY OF THE INVENTION

Therefore, with the foregoing in mind, it is an object of the present invention to provide new IS elements derived from Ralstonia solanacearum, which is one of the common pathogenic bacteria in vegetables. The Ralstonia solanacearum is a worldwide common soil infectious plant pathogenic bacterium that causes wilt vessel disease to more than 100 species of more than 30 families including Solanaceae plants such as tomatoes, tobacco and potatoes. It is another object of the present invention to provide transposases that are encoded by these IS elements. These IS elements and the transposases make it possible to prevent infection to Ralstonia solanacearum, for example, by effecting recombination so that the transposases are inactivated, which is very useful in the field of agriculture.

In order to achieve the above objects, the inventors of the present invention have succeeded in isolating new IS elements from Ralstonia solanacearum and realized the present invention.

The present invention provides an insertion sequence element or a functional equivalent thereof comprising: a base sequence of Sequence I.D. No.2 at the 5' terminal and a base sequence of Sequence I.D. No.3 at the 3'.terminal as terminal inverted repeat sequences; and a base sequence encoding amino acid sequences of Sequence I.D. Nos.4 and 5 as open reading frames between the terminal inverted repeat sequences. Herein, the open reading frame can be present overlapped or independently.

The present invention further provides an insertion sequence element consisting of the base sequence of Sequence I.D. No.1.

Furthermore, the present invention provides an insertion sequence element or a functional equivalent thereof comprising: a base sequence of Sequence I.D. No.7 at the 5' terminal and a base sequence of Sequence I.D. No.8 at the 3' terminal as terminal inverted repeat sequences; and a base sequence encoding amino acid sequences of Sequence I.D. Nos.9 and 10 as open reading frames between the terminal inverted repeat sequences. Herein, the open reading frame can be present overlapped or independently.

The present invention further provides an insertion sequence element consisting of a base sequence of Sequence I.D. No.6.

Furthermore, the present invention provides an insertion sequence element or a functional equivalent thereof comprising: a base sequence of Sequence I.D. No.12 at the 5' terminal and a base sequence of Sequence I.D. No.13 at the 3' terminal as terminal inverted repeat sequences; and a base sequence encoding an amino acid sequence of Sequence I.D. No.14 as an open reading frame between the terminal inverted repeat sequences.

The present invention further provides an insertion sequence element consisting of a base sequence of Sequence I.D. No.11.

The present invention further provides a transposase or a functional equivalent thereof expressed from a base sequence of positions 56 to 855 of Sequence I.D. No. 1.

The present invention further provides a transposase or a functional equivalent thereof expressed from a base sequence of positions 65 to 822 of Sequence I.D. No.6.

The present invention further provides a transposase or a functional equivalent thereof expressed from a base sequence of positions 44 to 865 of Sequence I.D. No.11.

It should be noted that "movable genetic elements" (transposable elements) such as transposons may be significantly involved in the evolution and the environmental adaptation of organisms as self-mechanism of self-alternation of the organism's genome. The gene of the present invention moves on the genome of microorganisms and has the nature of activating or inactivating the gene that is positioned downstream of the genome into which the gene of the present invention jumps. Utilizing this property, it is possible to isolate industrially useful genes efficiently.

Furthermore, utilizing these genes, it is possible to determine the infection route and identify the bacteria in regard to Ralstonia solanacearum. Furthermore, the transposition function of the transposable element is promoted by utilizing the transposases of the present invention, so that it is possible to isolate industrially useful genes efficiently. In addition, it is expected that protectant effects such as promotion of a reduction in the pathogenicity caused by the mutation induction of Ralstonia solanacearum can be provided.

These and other advantages of the present invention will become apparent to those skilled in the art upon reading and understanding the following detailed description with reference to the accompanying figures.

DESCRIPTION OF THE PREFERRED EMBODIMENT (1) Definitions

In the present invention, "IS element" refers to a gene unit that has a size of 2 kb or less, has no phenotypic gene other than genes involved in gene transposition, and includes one or two open reading frames encoding transposase and terminal inverted repeat sequences.

ISJsp104.2 is an IS element consisting of the base sequence of Sequence I.D. No.1.

ISmsp4.2 is an IS element consisting of the base sequence of Sequence I.D. No.6.

ISmsp101.3 is an IS element consisting of the base sequence of Sequence I.D. No.11.

In the present invention, "transposase" is an enzyme that catalyzes an insertion reaction of a gene.

A "functional equivalent" used in the present invention refers to an IS element or a transposase that substantially has the function or the activity of the original IS element or transposase, and has at least 90%, preferably at least 95% of homology in the base sequence or the amino sequence, respectively, when optimally aligned with the original IS element or transposase.

Such a functional equivalent of the IS element includes substitution, addition, deletion or insertion of at least one nucleotide, in addition to the original sequence in the terminal inverted repeat sequence or the open reading frame that is a functional site, and has at least functions or activities substantially equivalent to those of the original IS element or transposase. Examples of such a functional equivalent include IS elements having a nucleotide substitution that causes conservative substitution of the amino acid of the transposase to be encoded, and IS elements having an intervening nucleotide in the open reading frame.

Such a functional equivalent of transposase may include substitution of at least one amino acid (preferably conservative substitution), or additional amino acid (e.g., a reader sequence, a secretion sequence, and a sequence that would advantageously function in purification), in addition to the original sequence. It is appreciated that production of these functional equivalents is within a scope of technical knowledge that can be routinely obtained by those skilled in the art.

(2) Method for Searching a Transposable Element

In the search of a transposable element, molecular biological experiment techniques (electrophoresis of DNA, collection of electrophoresed DNA from a gel, digestion of restriction enzyme, PCR, labeling of DNA, hybridization, base sequencing and the like) can be used. Examples of these techniques include the techniques described in Sambrook et al., A Laboratory Manual, the second edition, Cold Spring Harbor Press, Cold Spring Harbor, N.Y. (1989) and other methods routinely used by those skilled in the art.

(a) Bacteria to be Used

In the present invention, Ralstonia solanacearum is used. A preferable strain is a Ralstonia solanacearum strain MAFF301556. This strain is a Ralstonia solanacearum isolated from a potato in Nagasaki in 1983. This strain is deposited as a distributable strain with the Gene Bank of the Ministry of Agriculture, Forestry and Fisheries (2-1-2, Kannondai, Tsukuba-shi, Ibaraki) and is available to anyone for test and research.

(b) Principle

A transposon trap vector is used as means for isolating a transposable element. In the present invention, pSHI1063 (Iida et al., Abstract of Proceeding of The fourteenth Conference of Molecule Biology Society of Japan, p.216 (1991)) is used as the transposon trap vector. The trap vector pSHI1063 has a full length of 11.5 kb, and is a fusion plasmid of the plasmid pVS1 with wide host range of Pseudomonas aeruginosa and the plasmid pBR322 of $E.$ $coli$. The trap vector pSHI1063 can be grown in a wide range of Gram-negative bacteria such as $E.$ $coli$, bacteria of the Pseudomonas genus, the Agrobacterium genus, the Rhizobium genus and the like. The trap vector pSHI1063 has an ampicillin-resistant gene and a spectinomycin-resistant gene as selective marker genes. In addition, in order to trap a transposable element, this trap vector has a cI repressor gene of λ phage and a kanamycin-resistant gene (neo) connected to a $P_R$ promoter that is under control of the cI repressor (this is called a trap cassette gene). After introducing the trap vector pSHI1063 to a bacterium, a transposable element such as an IS element of the bacterium transposes into the cI repressor gene in the trap vector pSHI1063. Then, the cI repressor in the trap vector is inactivated and the $P_R$ promoter is activated, so that the kanamycin-resistant gene operates. Therefore, when the transposable element is present in the cI repressor gene of the trap vector pSHI1063, the bacterium is resistant to kanamycin, and therefore the transposable element can be selected efficiently.

(c) Acquisition of the Transposable Element

Based on the above principle, the trap vector pSHI1063 is introduced to a Ralstonia solanacearum strain MAFF301556, and a selected kanamycin-resistant strain is cultured, and boiled, for example, at 100° C. for 5 minutes so that the bacterial cells are lysed, and the DNA is extracted. Then, PCR is performed using the sequence of the trap cassette gene as the primer so as to amplify a DNA fragment having a transposable element (Sambrook et al., ibid.).

(d) Base Sequencing of the Transposable Element

Next, the base sequence of the amplified and collected insertion sequence is determined. First, an intended DNA fragment is prepared from a product of the PCR amplification including the transposable element obtained in (c), and is subcloned into an appropriate vector, for example, a pT7Blue vector. A plasmid DNA is prepared from the obtained positive clone, and is used as a template for base sequencing. Thus, this plasmid DNA is sequenced on both strands, for example, by primer walking method. For sequencing, an autosequencer (model 1377 manufactured by ABI Corp.) can be used for example.

(e) Homology Search of the Isolated Transposable Element

A database (DNA Information and Stock Center, URL=is searched for the base sequence homology and the amino acid homology of the base sequenced transposable element, and a novel gene is characterized. In this manner, the transposable element is selected.

EXAMPLES

Hereinafter, the present invention will be described by way of examples.

Example 1

Search for a transposable element of a Ralstonia solanacearum strain MAFF301556 (hereinafter, referred to simply as "strain MAFF301556") was performed. To search the transposable element, a transposon trap vector is required, and in the present invention, pSHI1063 was used.

First, the strain MAFF301556 was grown on PTYG agar medium (0.25 g of bactopeptone, 0.25 g of bactotryptone, 0.5 g of bacto-yeast extract, 0.5 g of glucose, 30 mM of $MgSO_4.7H_2O$, 3.5 mg of $CaCl_2.2H_2O$, and 15 g of agar powder in 1000 ml of distilled water) at 28° C. The grown colony was inoculated into a 5 ml of a PTYG liquid medium and was cultured with shaking at 28° C. for 2 days.

Competent cells were made from this culture solution. Four ml of the culture solution were added to 200 ml of the PTYG medium, and cultivation was performed with shaking at 28° C. until the $OD_{500}$ reaches about 0.2. After cultivation, the culture solution was placed in ice for 20 minutes and then centrifuged (3000 rpm/10 min/4° C.) so as to collect bacterial pellets. The pellets were suspended in 10 ml of an ice-cold 1mM HEPES.NaOH buffer (pH 7.0). Then, the suspension was centrifuged again to collect bacterial pellets, and the pellets were suspended in 10 ml of an ice-cold 1 mM HEPES.NaOH buffer (pH 7.0). Then, the bacterial pellets were collected by centrifugation (8000 rpm/10 min/4° C.), and were suspended in 2 ml of an ice-cold 10% glycerol solution, so that competent cells were prepared.

Then, 40 μl of the obtained competent cells were mixed with about 0.36 μg of a transposon trap vector pSHI1063 (a liquid volume of 1 μl) dissolved in a TE buffer (10 mM Tris.HCl (pH8.0)–1 mM EDTA) and the mixture was transferred to a cuvette that was previously cooled to 4° C. Electric pulses were applied to this cuvette with a high voltage pulse generator, "Gene Pulser" manufactured by Biorad Co. The parameters for the electric pulse were an electrical resistance of 200Ω, an electrical capacity of 25 μFD, and an electric field of 6.25 KV/cm.

After applying pulses, a cell/DNA mixture was immediately transferred to 2 ml of the PTYG medium, and was cultured with shaking at 28° C. for one hour, followed by centrifugation (8000 rpm/10 min/4° C.). Then, bacterial pellets were suspended in 1 ml of sterilized distilled water. The suspension was serial diluted by a factor of 10 with sterilized distilled water sequentially, and diluted solutions with bacterial cells of up to $10^{-4}$ were obtained. Then, 100 µl of the diluted solutions were plated onto PIYG agar plates containing 100 µg/ml of spectinomycin. Further, the same number of bacterial cells was plated onto a PTYG agar plate that did not contain any antibodies as the control to check the transformation frequency, followed by culturing at 28° C. for 2 days. The transformed colonies resistant to spectinomycin that appeared were applied to a PIYG plate containing spectinomycin again with a platinum loop, and were cultured at 28° C. for 2 days, so that a single colony was formed. The transformation frequency of pSHI1063 to the Ralstonia solanacearum strain MAFF 301556 was $5 \times 10^{-4}$.

Figure 1:
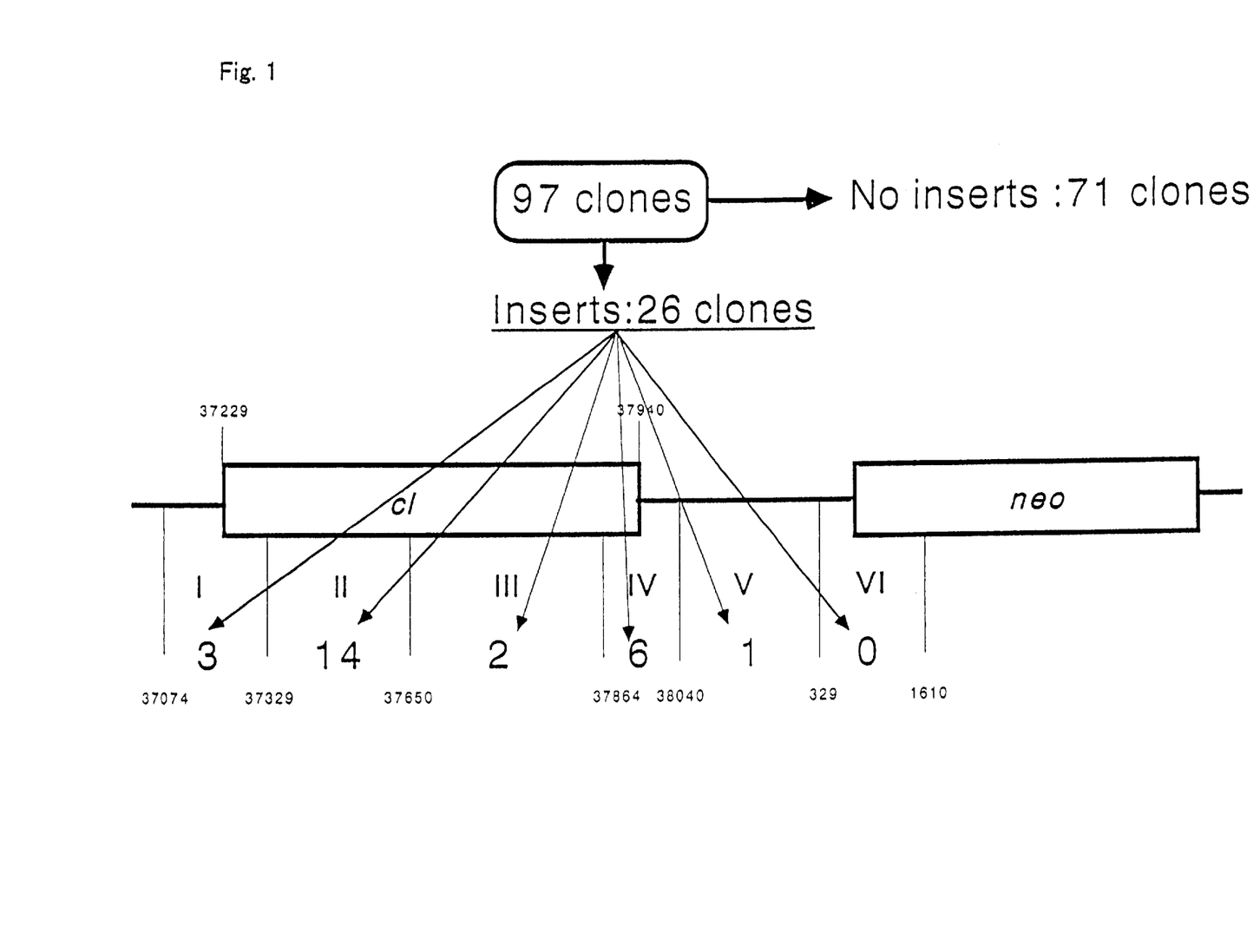
FIG. 1 is a diagram showing insertion positions of insertion sequences of 26 clones.
Figure 2:
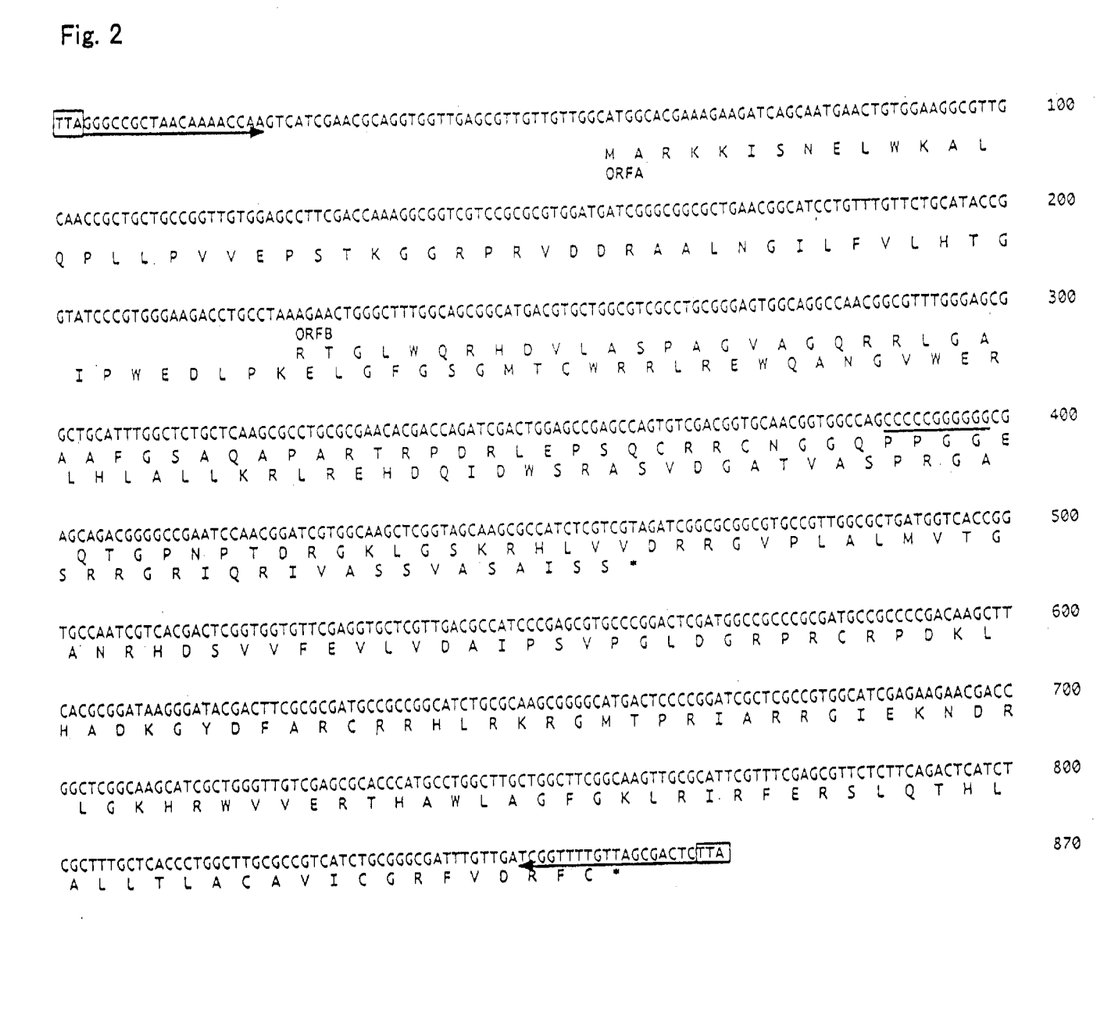
FIG. 2 is a diagram showing the positional relationship between ISJsp104.2 and an incomplete inverted sequence, a targeted overlapping sequence, ORFA and ORFB (SEQ ID NO: 1, with an additional TTA at each end, and SEQ ID NOS: 4–5).

Next, the spectinomycin-resistant colonies that formed a single colony were picked up one by one with a platinum loop and inoculated into 5 ml of a PTYG medium containing 100 µg/ml of spectinomycin, followed by culturing with shaking at 28° C. for 2 days. After cultivation, the suspension was serially diluted by a factor of 10 with sterilized distilled water. Then, 100 μl of the diluted solutions with the bacterial cells ranging from an undiluted solution of the suspension to a $10^{-6}$ diluted solution were applied onto PTYG agar plates containing 50 μg/ml of kanamycin and 100 μg/ml of spectinomycin. Further, the same number of bacterial cells was plated onto a PTYG agar plate containing 100 μg/ml of spectinomycin as the control to check the appearance frequency of mutants, followed by culturing at 28° C. for 2 days. The obtained transformed colonies resistant to kanamycin were applied to a PTYG plate containing 50 μg/ml of kanamycin and 100 μg/ml of spectinomycin again with a platinum loop, so that a single colony was formed.

The appearance frequency of mutants from the obtained transformants ranged widely from about 100% to $6\times10^{-7}$, and was significantly different depending on the transformed clone. Ninety-seven mutants obtained from these transformants were used for the following examinations.

With respect to the 97 mutants, the DNA fragments of the insertion sequence were amplified by a PCR technique using various primers prepared based on the trap cassette gene sequence of pSHI1063 by routine procedures. For amplification, using a DNA amplifier (PC800 manufactured by ASTEC Inc.), a cycle of DNA denaturation at 94° C. for 1 minute, annealing at 55° C. for 2 minutes, and DNA elongation at 72° C. for 3 minute was repeated 25 times. After a PCR reaction, 1 μl of the reaction solution was used for agarose electrophoresis (1.5% agarose) to confirm the DNA amplification.

As a result, it was confirmed that DNA insertion was not observed in the plasmids of 71 kanamycin resistant mutants, whereas DNA fragments were inserted in the trap vectors pSHI1063 in the plasmids obtained from 26 mutants. The trap cassette gene of pSHI1063 was divided into 6 regions from the upstream to the downstream (divided into I to VI regions from the uppermost stream region of the cI gene to the upstream of the neo gene), and it was investigated into which region the DNA was inserted. The results were region I for 3 mutants, region II for 14 mutants, region III for 2 mutants, region IV for 6 mutants, region V for 1 mutant, and region VI for none (FIG. 1).

Next, the base sequences of the plasmids obtained from the 26 mutants were determined. The PCR reaction products were subcloned into pT7Blue vectors. Plasmid DNAs were prepared from the obtained positive clones and used as templates for base sequencing. These plasmid DNAs were sequenced on both strands, for example by primer walking with an autosequencer (model 1377 manufactured by ABI Corp.) (Sambrook et al., ibid).

With respect to the sequenced DNA fragments, a public database (DNA Information and Stock Center, was searched for base sequence homology and amino acid sequence homology, and the genes were characterized. Table 1 shows the results.

TABLE 1

The characteristics of DNA inserted in the pSHI1063 trap cassette

| No. | Clone | Deduced size | Insertion region | IS element |
|---|---|---|---|---|
| 1 | Jsp104.2 | 864 bp | I | ISJsp104.2 |
| 2 | Jsp105.1 | 1.2 kb | I | iso-IS1420 |
| 3 | Jsp101.5 | 1.2 kb | I | iso-IS1420 |
| 4 | msp101.3 | 884 bp | II | ISmsp101.3 |
| 5 | Jsp104.1 | 1.3 kb | II | |
| 6 | Jsp107.3 | 1.2 kb | II | iso-IS1420 |
| 7 | Jsp107.4 | 1.2 kb | II | iso-IS1420 |
| 8 | Jsp105.5 | 1.2 kb | II | iso-IS1420 |
| 9 | Jsp120.5 | 1.2 kb | II | iso-IS1420 |
| 10 | Jsp120.1 | 1.2 kb | II | iso-IS1420 |
| 11 | Jsp101.2 | 1.2 kb | II | iso-IS1420 |
| 12 | Jsp102.3 | 1.0 kb | II | |
| 13 | Jsp101.4 | 1.2 kb | II | iso-IS1420 |
| 14 | Jsp105.3 | 1.2 kb | II | iso-IS1420 |
| 15 | Jsp120.2 | 1.2 kb | II | iso-IS1420 |
| 16 | Jsp120.3 | 1.2 kb | II | iso-IS1420 |
| 17 | Jsp120.4 | 1.2 kb | II | iso-IS1420 |
| 18 | msp4.4 | 0.8 kb | III | |
| 19 | Jsp105.2 | 0.8 kb | III | |
| 20 | msp101.5 | 1131 bp | IV | IS 1420 |
| 21 | msp 4.2 | 842 bp | IV | ISmsp 4.2 |
| 22 | Jsp102.1 | 1.2 kb | IV | iso-IS1420 |
| 23 | Jsp107.1 | 1.2 kb | IV | iso-IS1420 |
| 24 | Jsp104.3 | 0.2 kb | IV | |
| 25 | Jsp105.4 | 1.2 kb | IV | iso-IS1420 |
| 26 | Jsp107.2 | 1.2 kb | V | iso-IS1420 |

As a result, three novel IS elements (ISJsp104.2, ISmsp4.2 and ISmsp101.3) were isolated as the transposable elements. Their properties are as follows.

(a) ISJsp104.2

ISJsp104.2 is a base sequence with a full length of 864 bp composed of the base sequence of Sequence I.D. No.1, and has incomplete inverted repeat sequences (19 bp) at its terminals (the underlined arrow portion of FIG. 2, Sequence I.D. Nos. 2 and 3). Targeted overlapping sequences of 3 bp are coupled to both terminals of ISJsp104.2, and the sequence was TTA (the squared portions in FIG. 2). In comparison with the homology of the base sequence, ISJsp104.2 has a high homology of 74.8% with IS1418 (*Burkholderia glumae*), 70.9% with ISB111 (*Ralstonia solanacearum*) and 59.5% with IS402 (*Burkholderia cepacia*), which are IS elements belonging to the IS427 subgroup of the IS5 family (Mahillon et al., ibid.). Therefore, it seems that ISJsp104.2 is a novel IS element obtained from Ralstonia solanacearum that belongs to the IS427 subgroup of the IS5 family.

(Transposase Encoded by ISJsp104.2)

The base sequence analysis and the amino acid sequence homology analysis of ISJsp104.2 were performed and it was confirmed that this IS element encoded transposase, as other IS elements. ISJsp104.2 has two open reading frames (ORFA, ORFB) that are believed to encode a transposase (transposable enzyme), as generally seen in the IS3 and the IS5 families (Mahillon et al., ibid.). These open reading frames partly overlap, and are frame shifted (FIG. 2). Furthermore, there is a characteristic motif ($C_5G_6$) that is estimated to be involved in the frame shift in the base sequence in the overlapped portion (the underlined portion in FIG. 2) (Iversen et al., Plasmid 32:46–54 (1994)). ORFA is composed of 134 amino acids (Sequence I.D. No. 4) and ORFB is composed of 211 amino acids (Sequence I.D. No. 5). The ORFA and the ORFB of ISJsp104.2 have homologies of at least 70% in the amino acid sequences with the ORFA and the ORFB of IS 1418, respectively.

(b) ISmsp4.2

ISmsp4.2 is a base sequence with a full length of 842 bp composed of Sequence I.D. No.6, and has incomplete inverted repeat sequences (18 bp) at its terminals (the underlined arrow portion of FIG. 3, Sequence I.D. Nos. 7 and 8). Targeted overlapping sequences of 3 bp are coupled to both terminals of ISmsp4.2, and the sequence is TAA (the squared portions in FIG. 3). In comparison with the homology in the base sequence, ISmsp4.2 has a high homology of 56.7% with IS427 (*Agrobacterium tumefaciens*) and 54.9% with IS298 (*Caulobacter crescentus*), which are IS elements belonging to the IS427 subgroup of the IS5 family (Mahillon et al., ibid.). Therefore, it seems that ISmsp4.2 is a novel IS element obtained from Ralstonia solanacearum that belongs to the IS427 subgroup of the IS5 family.

Both the ISmsp4.2 and the ISmsp104.2 belong to the IS427 subgroup of the IS5 family, but have a homology as low as 50% or less to each other.

(Transposase Encoded by ISmsp4.2)

Figure 3:
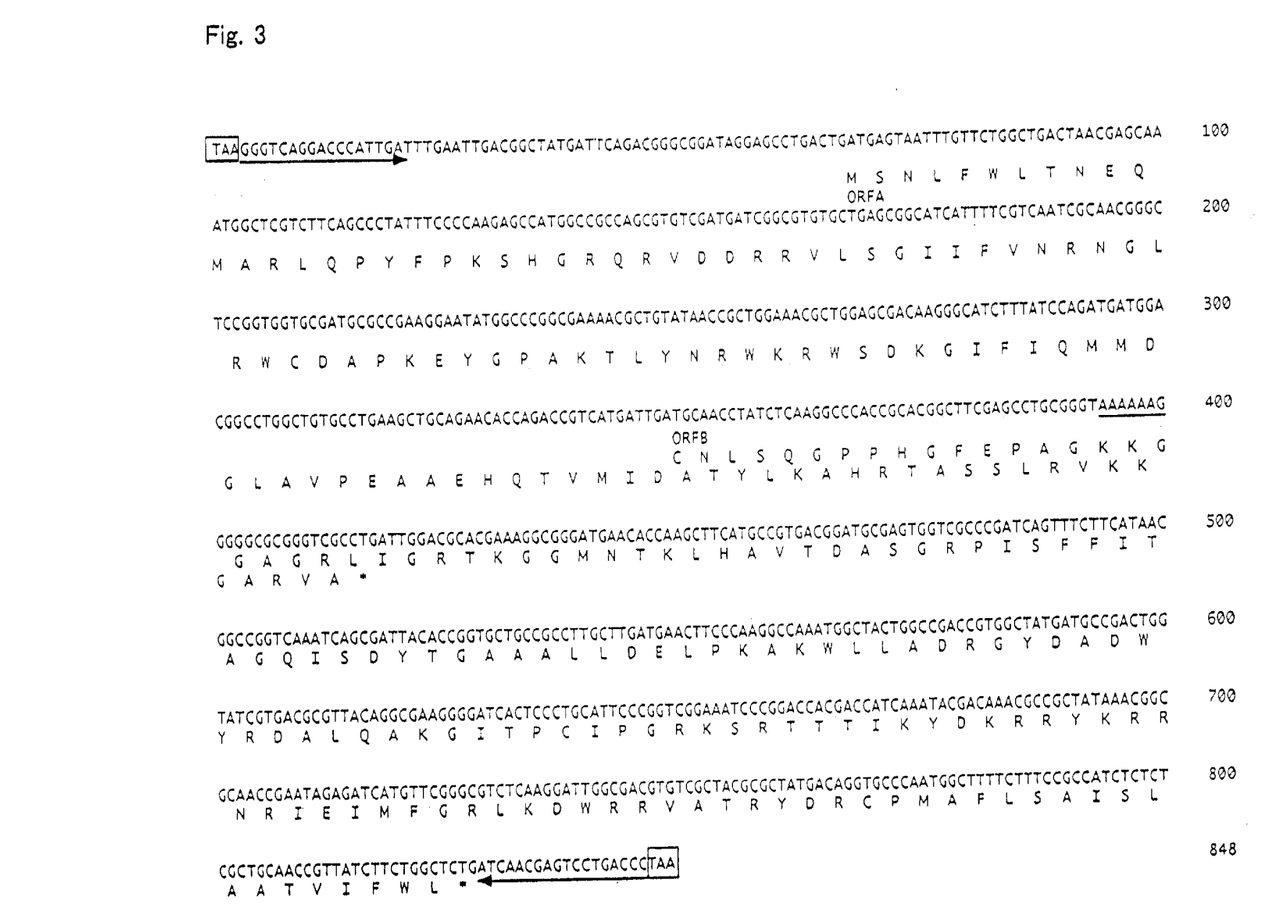
FIG. 3 is a diagram showing the positional relationship between ISmsp4.2 and an incomplete inverted sequence, a targeted overlapping sequence, ORFA and ORFB (SEQ ID NO: 6, with an additional TAA at each end, and SEQ ID NOS: 9–10).

Also ISmsp4.2 has two open reading frames, ORFA (116 amino acids) (Sequence I.D. No.9) and ORFB (159 amino acids) (Sequence I.D. No.10) that are believed to encode a transposase. As other IS elements that belong to the IS427 subgroup of the IS5 family, the ORFA and the ORFB partly overlap, and are frame shifted (FIG. 3). Furthermore, there is a characteristic motif ($A_6G$) that is estimated to be involved in the frame shift in the base sequence in the overlapped portion (the underlined portion in FIG. 3) (Ohtsubo and Sekine, ibid.). The ORFA and the ORFB do not have a high homology in the amino acid sequence with other IS elements, and the homologies are 40% or less in any cases.

(c) ISmsp101.3

Figure 4:
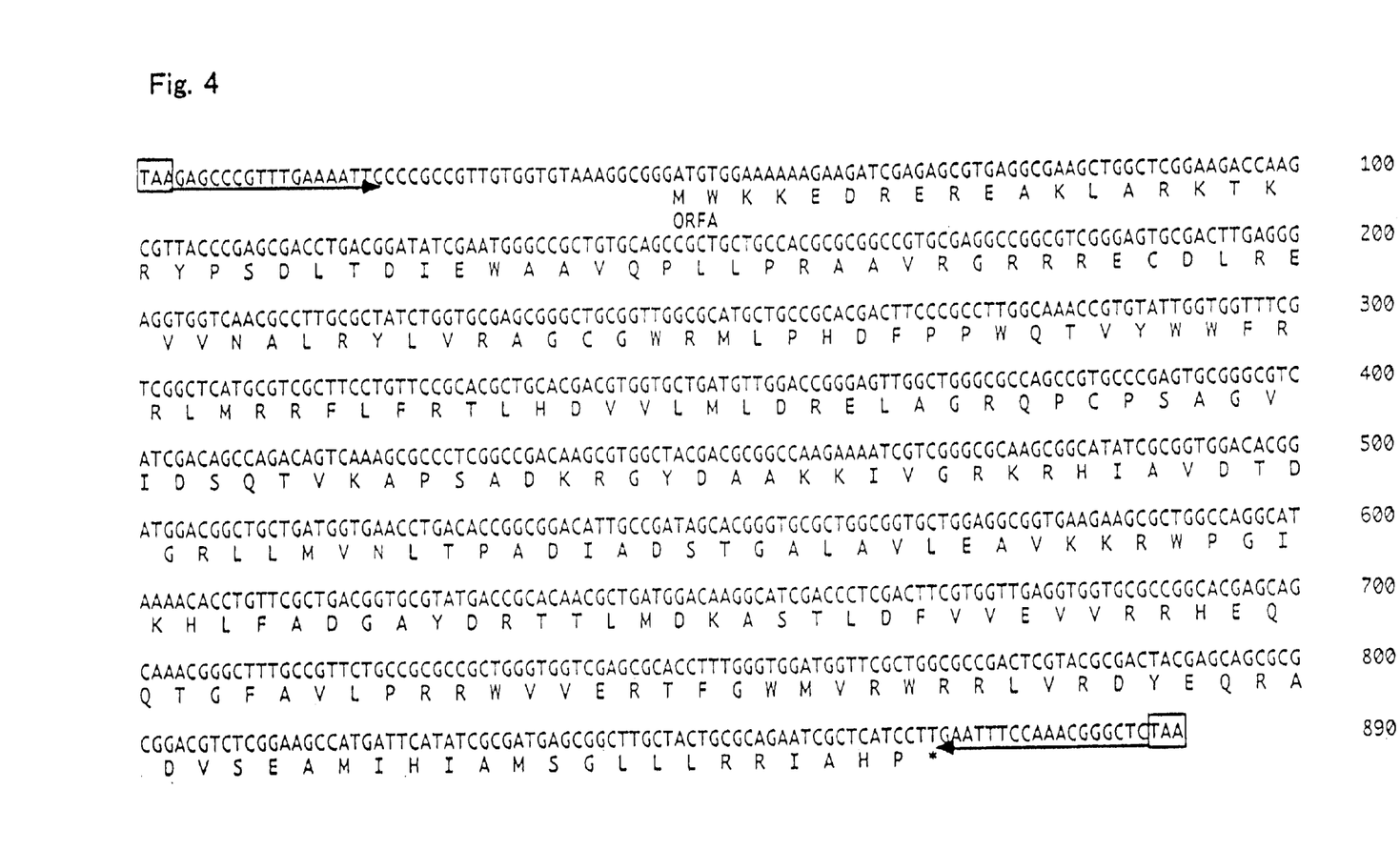
FIG. 4 is a diagram showing the positional relationship between ISmsp101.3 and an incomplete inverted sequence, a targeted overlapping sequence and ORFA (SEQ ID NO: 11, with an additional TAA at each end, and SEQ ID NO:14).

ISmsp101.3 is a base sequence with a full length of 884 bp composed of Sequence I.D. No.11, and has incomplete inverted repeat sequences (18 bp) at its terminals (the underlined arrow portion of FIG. 4, Sequence I.D. Nos.12 and 13). Targeted overlapping sequences of 3 bp are coupled to both terminals of ISmsp101.3, and the sequence is TAA (the squared portions in FIG. 4). In comparison with the homology in the base sequence, ISmsp101.3 has homologies of 67.6% with IS12528 (Gluconobacter suboxydans), 56.6% with ISR1F7–2 (*Rhizobium leguminosarum*), 56.5% with ISRm220-12-1 (*Sinorhizobium meliloti*) and 54.6% with IS1031 (*Acetobacter xylinum*), which are IS elements belonging to the IS1031 subgroup of the IS5 family (Mahillon et al., ibid.). Therefore, it is believed that ISmsp101.3 is a novel IS element obtained from Ralstonia solanacearum that belongs to the IS1031 subgroup of the IS5 family.

(Transposase encoded by ISmsp101.3)

Also ISmsp101.3 has an open reading frame, ORFA (274 amino acids) (Sequence I.D. No.14) that is believed to encode a transposase, and has a high homology in the amino acid sequence of 71.1% with the ORFA274 of IS12528, which belongs to the IS1031 subgroup of the IS5 family.

What is claimed is:

1. An isolated insertion sequence element or a functional equivalent thereof comprising:

the base sequence of SEQ ID NO: 12 at a 5' terminus and the base sequence of SEQ ID NO: 13 at a 3' terminus as terminal inverted repeat sequences; and a base sequence encoding the amino acid sequence of SEQ ID NO: 14 as an open reading frame between the terminal inverted repeat sequences.

2. An isolated insertion sequence element consisting of the base sequence of SEQ ID NO: 11.

* * * * *

SEQUENCE LISTING

<160> NUMBER OF SEQ ID NOS: 14

<210> SEQ ID NO 1
<211> LENGTH: 864
<212> TYPE: DNA
<213> ORGANISM: Ralstonia solanacearum

<400> SEQUENCE: 1

```
gggccgctaa caaaaccaag tcatcgaacg caggtggttg agcgttgttg ttggcatggc      60
acgaaagaag atcagcaatg aactgtggaa ggcgttgcaa ccgctgctgc cggttgtgga     120
gccttcgacc aaaggcggtc gtccgcgcgt ggatgatcgg gcggcgctga acggcatcct     180
gtttgttctg cataccggta tcccgtggga agacctgcct aaagaactgg gctttggcag     240
cggcatgacg tgctggcgtc gcctgcggga gtggcaggcc aacggcgttt gggagcggct     300
gcatttggct ctgctcaagc gcctgcgcga acacgaccag atcgactgga gccgagccag     360
tgtcgacggt gcaacggtgg ccagcccccg ggggcgagc agacggggcc gaatccaacg     420
gatcgtggca agctcggtag caagcgccat ctcgtcgtag atcggcgcgg cgtgccgttg     480
gcgctgatgg tcaccggtgc caatcgtcac gactcggtgg tgttcgaggt gctcgttgac     540
gccatcccga gcgtgcccgg actcgatggc cgcccgcgat gccgcccga caagcttcac       600 gcggataagg gatacgactt cgcgcgatgc cgccggcatc tgcgcaagcg gggcatgact     660
ccccggatcg ctcgccgtgg catcgagaag aacgaccggc tcggcaagca tcgctgggtt     720
gtcgagcgca cccatgcctg gcttgctggc ttcggcaagt tgcgcattcg tttcgagcgt     780
```

```
tctcttcaga ctcatctcgc tttgctcacc ctggcttgcg ccgtcatctg cgggcgattt    840
gttgatcggt tttgttagcg actc                                           864
```

<210> SEQ ID NO 2
<211> LENGTH: 19
<212> TYPE: DNA
<213> ORGANISM: Ralstonia solanacearum

<400> SEQUENCE: 2

```
gggccgctaa caaaaccaa                                                  19
```

<210> SEQ ID NO 3
<211> LENGTH: 19
<212> TYPE: DNA
<213> ORGANISM: Ralstonia solanacearum

<400> SEQUENCE: 3

```
tcggttttgt tagcgactc                                                  19
```

<210> SEQ ID NO 4
<211> LENGTH: 134
<212> TYPE: PRT
<213> ORGANISM: Ralstonia solanacearum

<400> SEQUENCE: 4

```
Met Ala Arg Lys Lys Ile Ser Asn Glu Leu Trp Lys Ala Leu Gln Pro
1               5                   10                  15
Leu Leu Pro Val Val Glu Pro Ser Thr Lys Gly Gly Arg Pro Arg Val
                20                  25                  30
Asp Asp Arg Ala Ala Leu Asn Gly Ile Leu Phe Val Leu His Thr Gly
            35                  40                  45
Ile Pro Trp Glu Asp Leu Pro Lys Glu Leu Gly Phe Gly Ser Gly Met
        50                  55                  60
Thr Cys Trp Arg Arg Leu Arg Glu Trp Gln Ala Asn Gly Val Trp Glu
65                  70                  75                  80
Arg Leu His Leu Ala Leu Leu Lys Arg Leu Arg Glu His Asp Gln Ile
                85                  90                  95
Asp Trp Ser Arg Ala Ser Val Asp Gly Ala Thr Val Ala Ser Pro Arg
            100                 105                 110
Gly Ala Ser Arg Arg Gly Arg Ile Gln Arg Ile Val Ala Ser Ser Val
        115                 120                 125
Ala Ser Ala Ile Ser Ser
    130
```

<210> SEQ ID NO 5
<211> LENGTH: 211
<212> TYPE: PRT
<213> ORGANISM: Ralstonia solanacearum

<400> SEQUENCE: 5

```
Arg Thr Gly Leu Trp Gln Arg His Asp Val Leu Ala Ser Pro Ala Gly
1               5                   10                  15
Val Ala Gly Gln Arg Arg Leu Gly Ala Ala Ala Phe Gly Ser Ala Gln
                20                  25                  30
Ala Pro Ala Arg Thr Arg Pro Asp Arg Leu Glu Pro Ser Gln Cys Arg
            35                  40                  45
Arg Cys Asn Gly Gly Gln Pro Pro Gly Gly Glu Gln Thr Gly Pro Asn
        50                  55                  60
```

Pro Thr Asp Arg Gly Lys Leu Gly Ser Lys Arg His Leu Val Val Asp
65                  70                  75                  80

Arg Arg Gly Val Pro Leu Ala Leu Met Val Thr Gly Ala Asn Arg His
            85                  90                  95

Asp Ser Val Val Phe Glu Val Leu Val Asp Ala Ile Pro Ser Val Pro
        100                 105                 110

Gly Leu Asp Gly Arg Pro Arg Cys Arg Pro Asp Lys Leu His Ala Asp
    115                 120                 125

Lys Gly Tyr Asp Phe Ala Arg Cys Arg Arg His Leu Arg Lys Arg Gly
130                 135                 140

Met Thr Pro Arg Ile Ala Arg Arg Gly Ile Glu Lys Asn Asp Arg Leu
145                 150                 155                 160

Gly Lys His Arg Trp Val Val Glu Arg Thr His Ala Trp Leu Ala Gly
                165                 170                 175

Phe Gly Lys Leu Arg Ile Arg Phe Glu Arg Ser Leu Gln Thr His Leu
            180                 185                 190

Ala Leu Leu Thr Leu Ala Cys Ala Val Ile Cys Gly Arg Phe Val Asp
        195                 200                 205

Arg Phe Cys
    210

<210> SEQ ID NO 6
<211> LENGTH: 842
<212> TYPE: DNA
<213> ORGANISM: Ralstonia solanacearum
<220> FEATURE:
<221> NAME/KEY: CDS
<222> LOCATION: (65)...(822)

<400> SEQUENCE: 6
gggtcaggac ccattgattt gaattgacgg ctatgattca gacgggcgga taggagcctg    60
actgatgagt aatttgttct ggctgactaa cgagcaaatg gctcgtcttc agccctattt   120
ccccaagagc catggccgcc agcgtgtcga tgatcggcgt gtgctgagcg gcatcatttt   180
cgtcaatcgc aacgggctcc ggtggtgcga tgcgccgaag aatatggccc ggcgaaaac    240 gctgtataac cgctggaaac gctggagcga caagggcatc tttatccaga tgatggacgg   300
cctggctgtg cctgaagctg cagaacacca gaccgtcatg attgatgcaa cctatctcaa   360
ggcccaccgc acggcttcga gcctgcgggt aaaaaagggg gcgcgggtcg cctgattgga   420
cgcacgaaag gcgggatgaa caccaagctt catgccgtga cggatgcgag tggtcgcccg   480
atcagtttct tcataacggc cggtcaaatc agcgattaca ccggtgctgc cgccttgctt   540
gatgaacttc ccaaggccaa atggctactg gccgaccgtg gctatgatgc cgactggtat   600
cgtgacgcgt tacaggcgaa ggggatcact ccctgcattc ccgtcggaa atcccggacc   660 acgaccatca aatacgacaa cgccgctat aaacggcgca accgaataga gatcatgttc   720
gggcgtctca aggattggcg acgtgtcgct acgcgctatg acaggtgccc aatggctttt   780
ctttccgcca tctctctcgc tgcaaccgtt atcttctggc tctgatcaac gagtcctgac   840
cc                                                                  842

<210> SEQ ID NO 7
<211> LENGTH: 17
<212> TYPE: DNA
<213> ORGANISM: Ralstonia solanacearum

<400> SEQUENCE: 7
gggtcaggac ccattga                                                       17

<210> SEQ ID NO 8
<211> LENGTH: 17
<212> TYPE: DNA
<213> ORGANISM: Ralstonia solanacearum

<400> SEQUENCE: 8
tcaacgagtc ctgaccc                                                       17

<210> SEQ ID NO 9
<211> LENGTH: 116
<212> TYPE: PRT
<213> ORGANISM: Ralstonia solanacearum

<400> SEQUENCE: 9

Met Ser Asn Leu Phe Trp Leu Thr Asn Glu Gln Met Ala Arg Leu Gln
1               5                   10                  15

Pro Tyr Phe Pro Lys Ser His Gly Arg Gln Arg Val Asp Asp Arg Arg
            20                  25                  30

Val Leu Ser Gly Ile Ile Phe Val Asn Arg Asn Gly Leu Arg Trp Cys
        35                  40                  45

Asp Ala Pro Lys Glu Tyr Gly Pro Ala Lys Thr Leu Tyr Asn Arg Trp
    50                  55                  60

Lys Arg Trp Ser Asp Lys Gly Ile Phe Ile Gln Met Met Asp Gly Leu
65                  70                  75                  80

Ala Val Pro Glu Ala Ala Glu His Gln Thr Val Met Ile Asp Ala Thr
                85                  90                  95

Tyr Leu Lys Ala His Arg Thr Ala Ser Ser Leu Arg Val Lys Lys Gly
            100                 105                 110

Ala Arg Val Ala
        115

<210> SEQ ID NO 10
<211> LENGTH: 159
<212> TYPE: PRT
<213> ORGANISM: Ralstonia solanacearum

<400> SEQUENCE: 10

Cys Asn Leu Ser Gln Gly Pro Pro His Gly Phe Glu Pro Ala Gly Lys
1               5                   10                  15

Lys Gly Gly Ala Gly Arg Leu Ile Gly Arg Thr Lys Gly Gly Met Asn
            20                  25                  30

Thr Lys Leu His Ala Val Thr Asp Ala Ser Gly Arg Pro Ile Ser Phe
        35                  40                  45

Phe Ile Thr Ala Gly Gln Ile Ser Asp Tyr Thr Gly Ala Ala Ala Leu
    50                  55                  60

Leu Asp Glu Leu Pro Lys Ala Lys Trp Leu Leu Ala Asp Arg Gly Tyr
65                  70                  75                  80

Asp Ala Asp Trp Tyr Arg Asp Ala Leu Gln Ala Lys Gly Ile Thr Pro
                85                  90                  95

Cys Ile Pro Gly Arg Lys Ser Arg Thr Thr Thr Ile Lys Tyr Asp Lys
            100                 105                 110

Arg Arg Tyr Lys Arg Arg Asn Arg Ile Glu Ile Met Phe Gly Arg Leu
        115                 120                 125

Lys Asp Trp Arg Arg Val Ala Thr Arg Tyr Asp Arg Cys Pro Met Ala
    130                 135                 140

-continued

```
Phe Leu Ser Ala Ile Ser Leu Ala Ala Thr Val Ile Phe Trp Leu
145                 150                 155

<210> SEQ ID NO 11
<211> LENGTH: 884
<212> TYPE: DNA
<213> ORGANISM: Ralstonia solanacearum
<220> FEATURE:
<221> NAME/KEY: CDS
<222> LOCATION: (44)...(865)

<400> SEQUENCE: 11
gagcccgttt gaaaattccc cgccgttgtg gtgtaaaggc gggatgtgga aaaaagaaga      60
tcgagagcgt gaggcgaagc tggctcggaa gaccaagcgt tacccgagcg acctgacgga     120
tatcgaatgg gccgctgtgc agccgctgct gccacgcgcg gccgtgcgag gccggcgtcg     180
ggagtgcgac ttgagggagg tggtcaacgc cttgcgctat ctggtgcgag cgggctgcgg     240
ttggcgcatg ctgccgcacg acttcccgcc ttggcaaacc gtgtattggt ggtttcgtcg     300
gctcatgcgt cgcttcctgt tccgcacgct gcacgacgtg gtgctgatgt tggaccggga     360
gttggctggg cgccagccgt gcccgagtgc gggcgtcatc gacagccaga cagtcaaagc     420
gccctcggcc gacaagcgtg gctacgacgc ggccaagaaa atcgtcgggc gcaagcggca     480
tatcgcggtg gacacggatg gacggctgct gatggtgaac ctgacaccgg cggacattgc     540
cgatagcacg ggtgcgctgg cggtgctgga ggcggtgaag aagcgctggc caggcataaa     600
acacctgttc gctgacggtg cgtatgaccg cacaacgctg atggacaagg catcgaccct     660
cgacttcgtg gttgaggtgg tgcgccggca cgagcagcaa acgggctttg ccgttctgcc     720
gcgccgctgg gtggtcgagc gcacctttgg gtggatggtt cgctggcgcc gactcgtacg     780
cgactacgag cagcgcgcgg acgtctcgga agccatgatt catatcgcga tgagcggctt     840
gctactgcgc agaatcgctc atccttgaat ttccaaacgg gctc                      884

<210> SEQ ID NO 12
<211> LENGTH: 18
<212> TYPE: DNA
<213> ORGANISM: Ralstonia solanacearum

<400> SEQUENCE: 12
gagcccgttt gaaaattc                                                    18

<210> SEQ ID NO 13
<211> LENGTH: 18
<212> TYPE: DNA
<213> ORGANISM: Ralstonia solanacearum

<400> SEQUENCE: 13
gaatttccaa acgggctc                                                    18

<210> SEQ ID NO 14
<211> LENGTH: 274
<212> TYPE: PRT
<213> ORGANISM: Ralstonia solanacearum

<400> SEQUENCE: 14

Met Trp Lys Lys Glu Asp Arg Glu Arg Glu Ala Lys Leu Ala Arg Lys
1               5                   10                  15

Thr Lys Arg Tyr Pro Ser Asp Leu Thr Asp Ile Glu Trp Ala Ala Val
            20                  25                  30
```

```
                    -continued

Gln Pro Leu Leu Pro Arg Ala Ala Val Arg Gly Arg Arg Arg Glu Cys
        35              40              45

Asp Leu Arg Glu Val Val Asn Ala Leu Arg Tyr Leu Val Arg Ala Gly
        50              55              60

Cys Gly Trp Arg Met Leu Pro His Asp Phe Pro Pro Trp Gln Thr Val
65              70              75              80

Tyr Trp Trp Phe Arg Arg Leu Met Arg Arg Phe Leu Phe Arg Thr Leu
                85              90              95

His Asp Val Val Leu Met Leu Asp Arg Glu Leu Ala Gly Arg Gln Pro
                100             105             110

Cys Pro Ser Ala Gly Val Ile Asp Ser Gln Thr Val Lys Ala Pro Ser
        115             120             125

Ala Asp Lys Arg Gly Tyr Asp Ala Ala Lys Lys Ile Val Gly Arg Lys
        130             135             140

Arg His Ile Ala Val Asp Thr Asp Gly Arg Leu Leu Met Val Asn Leu
145             150             155             160

Thr Pro Ala Asp Ile Ala Asp Ser Thr Gly Ala Leu Ala Val Leu Glu
                165             170             175

Ala Val Lys Lys Arg Trp Pro Gly Ile Lys His Leu Phe Ala Asp Gly
                180             185             190

Ala Tyr Asp Arg Thr Thr Leu Met Asp Lys Ala Ser Thr Leu Asp Phe
        195             200             205

Val Val Glu Val Val Arg Arg His Glu Gln Gln Thr Gly Phe Ala Val
        210             215             220

Leu Pro Arg Arg Trp Val Val Glu Arg Thr Phe Gly Trp Met Val Arg
225             230             235             240

Trp Arg Arg Leu Val Arg Asp Tyr Glu Gln Arg Ala Asp Val Ser Glu
                245             250             255

Ala Met Ile His Ile Ala Met Ser Gly Leu Leu Leu Arg Arg Ile Ala
                260             265             270

His Pro
```